(12) United States Patent
Piecuch

(10) Patent No.: US 10,857,002 B2
(45) Date of Patent: Dec. 8, 2020

(54) SECURING AN ACETABULAR COMPONENT TO AN ACETABULAR BONE

(71) Applicant: Zimmer, Inc., Warsaw, IN (US)

(72) Inventor: Cristina Piecuch, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 137 days.

(21) Appl. No.: 16/155,285

(22) Filed: Oct. 9, 2018

(65) Prior Publication Data

US 2019/0105177 A1    Apr. 11, 2019

Related U.S. Application Data

(60) Provisional application No. 62/570,314, filed on Oct. 10, 2017.

(51) Int. Cl.

| A61F 2/34 | (2006.01) |
|---|---|
| A61F 2/46 | (2006.01) |
| A61F 2/30 | (2006.01) |
| A61B 17/86 | (2006.01) |
| A61B 17/04 | (2006.01) |

(52) U.S. Cl.
CPC ........ *A61F 2/4609* (2013.01); *A61F 2/30749* (2013.01); *A61F 2/34* (2013.01); *A61B 17/0401* (2013.01); *A61B 17/86* (2013.01); *A61F 2/4644* (2013.01); *A61F 2002/30462* (2013.01); *A61F 2002/30535* (2013.01); *A61F 2002/30736* (2013.01); *A61F 2002/3401* (2013.01); *A61F 2250/0058* (2013.01)

(58) Field of Classification Search
CPC ...... A61F 2/4609; A61F 2/34; A61F 2/30749; A61F 2002/3479
USPC ............................................ 623/22.36, 22.37
See application file for complete search history.

(56) References Cited

U.S. PATENT DOCUMENTS

| 8,298,262 B2 | 10/2012 | Stone et al. | |
|---|---|---|---|
| 8,361,113 B2 | 1/2013 | Stone et al. | |
| 9,474,613 B2 | 10/2016 | Kurtz | |
| 2002/0042654 A1* | 4/2002 | Masini | A61F 2/34 623/22.32 |
| 2013/0006276 A1* | 1/2013 | Lantz | A61B 17/0467 606/144 |
| 2013/0066437 A1* | 3/2013 | Weeden | A61F 2/34 623/22.36 |

(Continued)

*Primary Examiner* — Bruce E Snow
(74) *Attorney, Agent, or Firm* — Schwegman Lundberg & Woessner, P.A.

(57) ABSTRACT

A surgeon can secure an acetabular component to an acetabular bone. The surgeon can insert a pair of anchors through a corresponding pair of holes in the acetabular component into a corresponding pair of pilot holes drilled into the acetabular bone. Each anchor is attached to a length of suture before insertion. The surgeon can tie the sutures from the anchors together, to secure the acetabular component against the acetabular bone. The surgeon can position the tied lengths of suture in a suture channel formed in the acetabular component. The suture channel can prevent the suture from interfering with a liner that contacts the acetabular component. The surgeon can repeat as needed, using multiple pairs of anchors, multiple holes and suture channels in the acetabular component, and multiple pilot holes in the acetabular bone. The surgeon can use soft anchors or screw anchors.

19 Claims, 8 Drawing Sheets

(56) References Cited

U.S. PATENT DOCUMENTS

| | | | |
|---|---|---|---|
| 2013/0204388 A1* | 8/2013 | Meridew | A61F 2/34 623/22.36 |
| 2014/0031863 A1* | 1/2014 | Gittings | A61B 17/0401 606/232 |
| 2017/0027703 A1 | 2/2017 | Kurtz | |

* cited by examiner

SECURING AN ACETABULAR COMPONENT TO AN ACETABULAR BONE

CLAIM OF PRIORITY

This application claims the benefit of U.S. Provisional Patent Application Ser. No. 62/570,314, filed on Oct. 10, 2017, the benefit of priority of which is claimed hereby, and which is incorporated by reference herein in its entirety.

TECHNICAL FIELD

The present disclosure relates to a device for securing an acetabular component to an acetabular bone during hip replacement surgery. The acetabular component can include a shell, a shell/augment construct, an augment, a shell/cage construct, or a cage.

BACKGROUND

The acetabulum is a concave surface of the pelvis. The head of the femur meets with the pelvis at the acetabulum, forming the hip joint. In total or partial hip replacement surgery, one or more components of the hip joint are replaced with artificial components. There is ongoing effort to improve the reliability and lifetime of these artificial components, and the manner in which they are installed.

BRIEF DESCRIPTION OF THE DRAWINGS

The present disclosure is illustrated by way of example and not limitation in the figures of the accompanying drawings, in which like reference numbers indicate similar elements.

DETAILED DESCRIPTION

Figure 1:
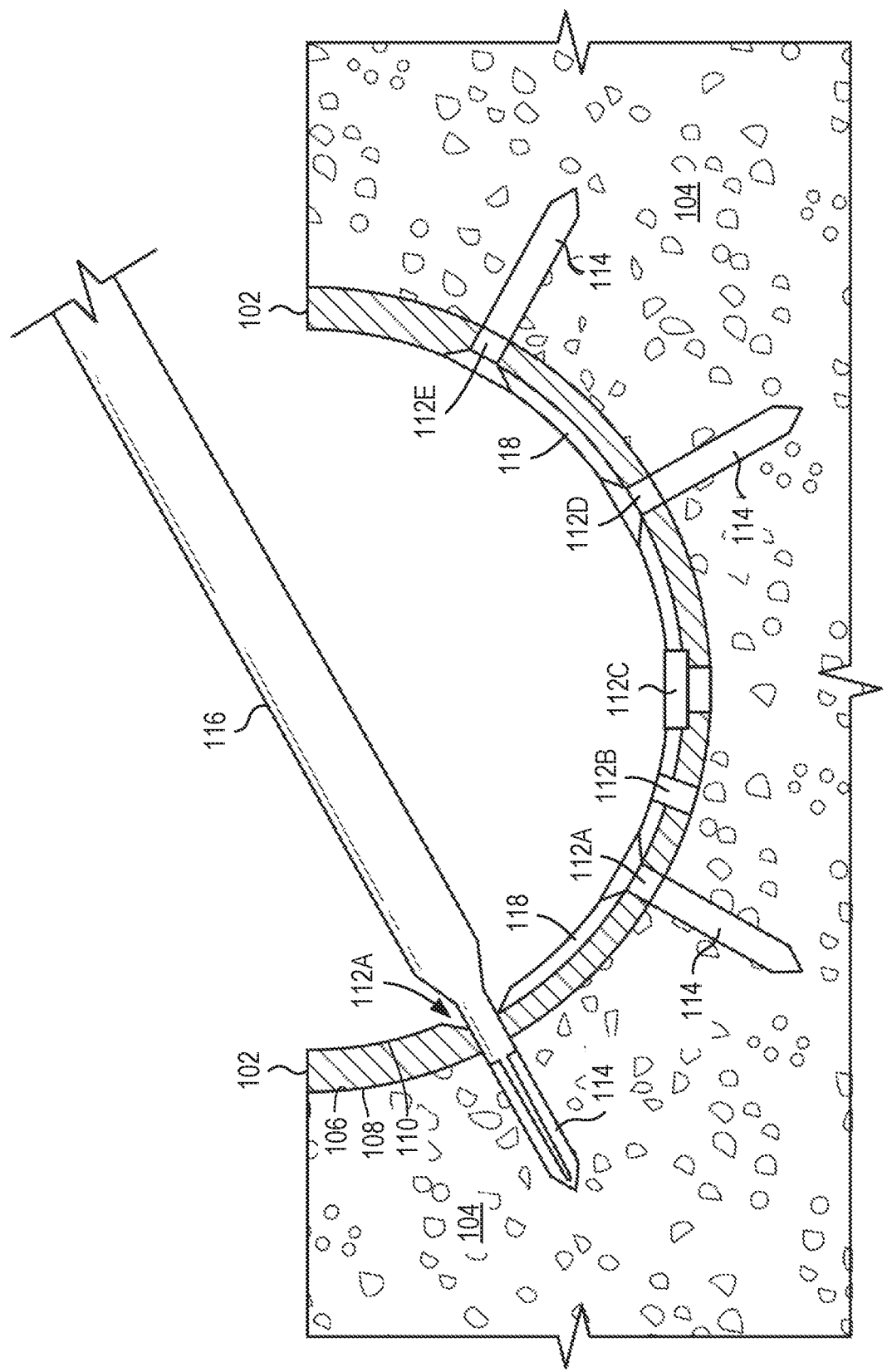
FIG. 1 shows a side-view cross-section of an example of an acetabular component positioned in contact with acetabular bone, in accordance with some examples.

During hip replacement surgery, a surgeon can shape a portion of the acetabular bone to have a concave surface, then attach an acetabular component to the concave surface of the acetabular bone. The acetabular component can include a shell, a shell/augment construct, an augment, a shell/cage construct, or a cage. In some examples, the acetabular component can be formed from metal, and can structurally support other elements in the replacement hip joint.

The acetabular component can be cup-shaped. The acetabular component can have a convex outer surface that can face the concave surface of the acetabular bone when installed. The acetabular component can have a concave inner surface that can face a convex outer surface of a polymer, ceramic, or metal liner when installed. In some examples, the polymer, ceramic, or metal liner can be cemented inside the acetabular component. The polymer, ceramic, or metal liner can have a concave inner surface in which a femoral head can articulate (or have sliding contact) in the replacement hip joint (forming a ball-in-joint socket) when installed in a modular total hip arthroplasty. The components of the hip joint can be arranged to prevent metal-to-metal contact as components move with respect to one another.

A surgeon can secure the acetabular component to the acetabular bone, using the techniques discussed in detail below. Two such techniques are summarized in the following three paragraphs.

In one example, a surgeon can insert a pair of anchors through a corresponding pair of holes in the acetabular component into a corresponding pair of pilot holes drilled into the acetabular bone. Each anchor is attached to a length of suture before insertion. The surgeon can tie the sutures from the anchors together, to secure the acetabular component against the acetabular bone. At the location at which the sutures connect, the sutures can form a knot. Alternatively, particularly for metallic sutures, the sutures can be twisted or clamped together. The surgeon can position the tied-together portions of suture in a suture channel formed in the acetabular component. The suture channel can prevent the suture from interfering with the polymer, metal, or ceramic liner that contacts the acetabular component. The surgeon can repeat as needed, using multiple pairs of anchors, multiple holes and multiple suture channels in the acetabular component, and multiple pilot holes in the acetabular bone. The anchors can be soft anchors or screw anchors.

In another example, a surgeon can insert a soft anchor through a hole in the acetabular component into a corresponding pilot hole drilled into the acetabular bone. The soft anchor is attached to a length of suture before insertion. The surgeon can tie at least a portion of the length of suture around a rim feature positioned around the hole in the acetabular component, to secure the acetabular component against the acetabular bone. The rim feature in the acetabular component can prevent the suture from interfering with the polymer, metal, or ceramic liner that contacts the acetabular component. The surgeon can repeat as needed, using multiple soft anchors, multiple holes with rim features in the acetabular component, and multiple pilot holes in the acetabular bone.

The two techniques can be used independently, or optionally can be combined on a single acetabular component. In each of the techniques discussed below, the pilot holes in the acetabular bone can be drilled into, but not through, the acetabular bone. Drilling the pilot holes so that they don't extend fully through the acetabular bone can maintain the structural integrity of the acetabular bone, which could otherwise be compromised by drilling one or more pilot holes through the acetabular bone. Using pilot holes that do not fully extend through the acetabular bone can reduce or eliminate the risk of soft tissue, organ, or nerve damage, and/or blood vessel puncture.

The above three paragraphs are merely summaries of techniques that can secure an acetabular component to an acetabular bone, and should not be construed as limiting in any way. These and other techniques are discussed below in further detail.

FIG. 1 shows a side-view cross-section of an example of an acetabular component 102 positioned in contact with acetabular bone 104, in accordance with some examples. In the example of FIG. 1, the acetabular component 102 is an acetabular shell. As explained below, other types of acetabular components can also be used.

The acetabular component 102 can be cup-shaped. The acetabular component 102 can have a convex outer surface 106 that can face a concave surface 108 of the acetabular bone 104 when installed. The acetabular component 102 can have a concave inner surface 110 that can face a convex outer surface of a polymer, metal, or ceramic liner (not shown) when installed. The liner can be cemented inside the acetabular component 102, e.g., against the concave inner surface 110 of the acetabular component 102. An inner surface of the liner can provide an interface to contact a corresponding moving part in the hip joint.

The acetabular component 102 can include various holes 112A-E that can extend through the acetabular component 102, from the concave inner surface 110 to the convex outer surface 106. During a procedure, a surgeon can insert an anchor through a hole 112A-E into the acetabular bone 104, which can secure the acetabular component 102 to the acetabular bone 104, The surgeon can insert multiple anchors through respective holes 112A-E in the acetabular component 102, as needed, to achieve sufficient fixation of the acetabular component 102.

Each hole 112A-E can have one of a plurality of configurations, depending on what type of anchor the hole 112A-E is intended to accommodate.

For example, a hole 112A, 112C, 112D, 112E that is intended to accommodate a screw anchor can have a countersink that extends into the concave inner surface 110 of the acetabular component 102. The countersink can be angled, as in holes 112A, 112D, and 112E, or can be sunk in a portion parallel to the hole, as in hole 1120. When the screw anchor is fully inserted into the acetabular bone 104, a head of the screw anchor can be positioned in the countersink, so that the screw anchor does not interfere with the liner.

As another example, a hole 112B that is intended to accommodate a soft anchor (e.g., an anchor that can deform when inserted) may lack such a countersink. In some examples, such a hole 112B can extend cylindrically through the acetabular component 102 with a uniform cross-sectional size from the concave inner surface 110 to the convex outer surface 106.

The holes 112A-E in the acetabular component 102 can be positioned in specified locations, so that they can coincide with corresponding pilot holes 114 in the acetabular bone 104. In some examples, a surgeon can drill one or more of the pilot holes 114 in the acetabular bone 104, either using a drill guide, or without using a drill guide. The pilot holes 114 can accommodate a soft anchor or a screw anchor. In some examples, a hole in the acetabular bone 104 can be sized and shaped as needed.

After the surgeon has drilled the pilot holes 114 in the acetabular bone 104 and positioned the acetabular component 102 on the acetabular bone 104 so that the holes 112A-E in the acetabular component 102 align with the pilot holes 114 in the acetabular bone 104, the surgeon can insert the anchors into the suitable holes.

The surgeon can insert screw anchors using a screwdriver (not shown) having a suitable driver configuration, such as a hex head, Philips head or other suitable configuration.

The surgeon can insert soft anchors using an elongated insertion tool 116. In some examples, a soft anchor can be pre-installed on a distal end of the insertion tool 116. The surgeon can grip a proximal portion of the insertion tool 116, insert the soft anchor into the hole, retract the insertion tool 116, and leave the soft anchor in the pilot hole 114. In some examples, each soft anchor can be provided pre-installed on its own single-use insertion tool. In other examples, the surgeon or a technician can load the soft anchors as needed onto a multi-use insertion tool.

Each anchor can be attached to one or more lengths of suture. After a surgeon attaches an anchor to the acetabular bone 104, through a hole 112A-E in the acetabular component 102, the length of suture can extend out of the hole 112A-E in the acetabular component 102. In some examples, the surgeon can tie together the sutures from adjacent holes. Tying the lengths of suture together can secure the acetabular component 102 against the acetabular bone 104. The surgeon can then position the tied-together lengths of suture in one or more suture channels 118 formed in the acetabular component 102. The suture channels 118 in the acetabular component 102 can position the tied-together lengths of suture parallel to the concave inner surface 110 of the acetabular component 102 but below the concave inner surface 110, which can prevent the tied-together lengths of suture from interfering with the liner.

In the configuration of FIG. 1, the acetabular component 102 is an acetabular shell. Other acetabular components 102 can also be used. For example, for revisions or complex primary cases in which there is a defect in the acetabular bone 104 such as an acetabular discontinuity, the surgeon can use an acetabular cage. Additionally, the surgeon can optionally use one or more acetabular augments, for regions in which the acetabular bone 104 has deteriorated. In some examples, the acetabular cage can be placed in direct contact with the acetabular bone 104, and a polymer or metal liner or cup can be cemented inside of the acetabular cage. In other examples, the acetabular cage can be positioned on top of an acetabular shell, so that at least a portion of the acetabular shell is positioned between at least a portion of the acetabular cage and the acetabular bone 104.

Figure 2:
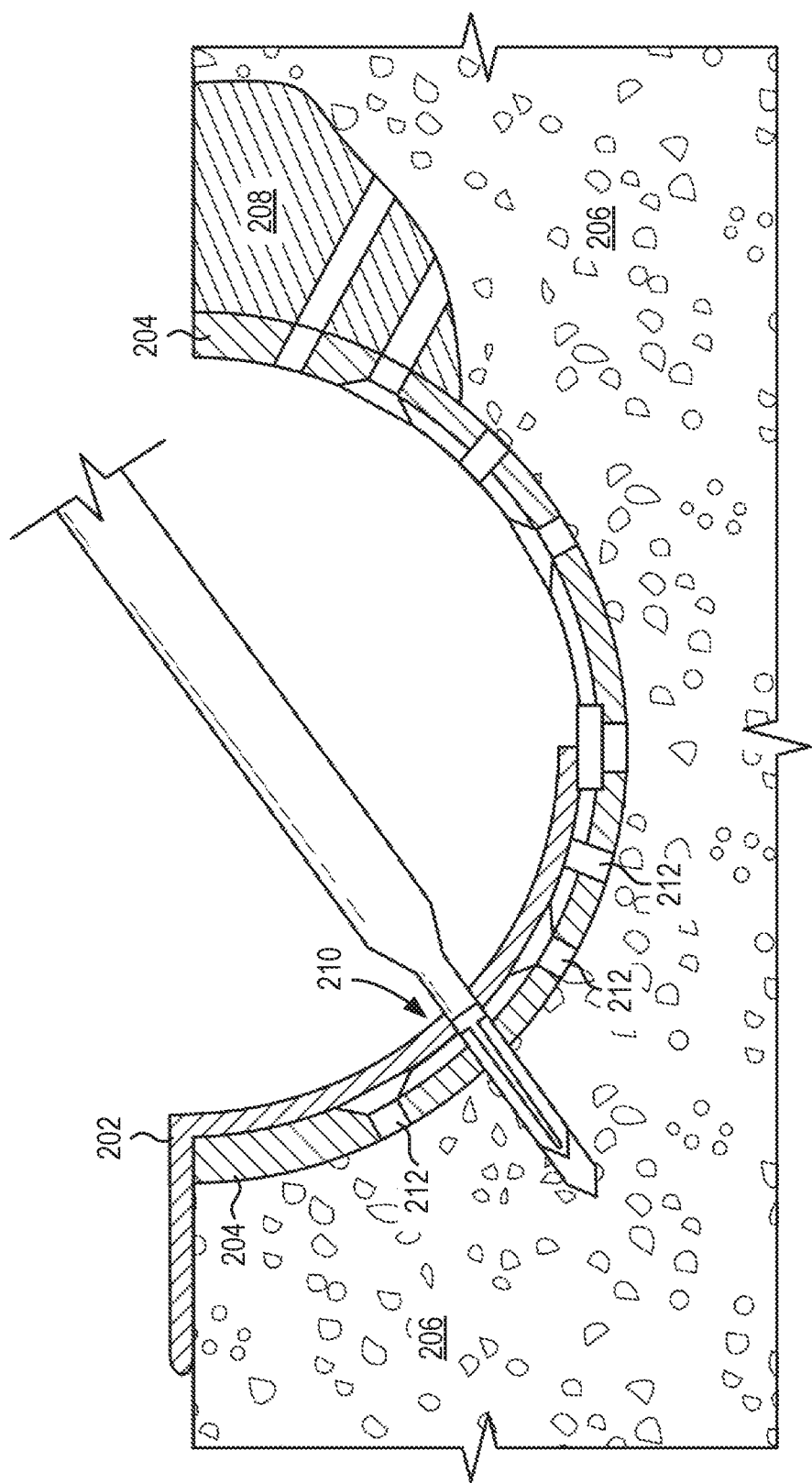
FIG. 2 shows a side-view cross-section of an example of an optional acetabular cage positioned between an acetabular shell and acetabular bone, and an example of an optional acetabular augment positioned between a portion of the acetabular shell and a portion of the acetabular bone, in accordance with some examples.

FIG. 2 shows a side-view cross-section of an example of an optional acetabular cage 202 positioned between an acetabular shell 204 and acetabular bone 206, and an example of an optional acetabular augment 208 positioned between a portion of the acetabular shell 204 and a portion of the acetabular bone 206, in accordance with some examples. It will be understood that the acetabular shell 204, the acetabular cage 202, and the acetabular augment 208 can be used singularly, in any paired combination, or all together, as needed.

The left-hand portion of FIG. 2 shows the acetabular cage 202 positioned on top of (e.g., inside) the acetabular shell 204, which is in turn positioned on top of (e.g., inside) the acetabular bone 206. Typically, for a metal acetabular shell 204, the corresponding acetabular cage 202 can be positioned inside the acetabular shell 204, although the acetabular cage 202 can alternatively be positioned outside the acetabular shell 204.

In some examples, the acetabular cage 202 can include one or more holes 210 that align with corresponding pilot holes in the acetabular shell 204. When an anchor is inserted through these holes 210, the suture can extend through both the acetabular cage 202 and the acetabular shell 204. In other examples, the acetabular shell 204 can include one or more holes 212 that do not have a corresponding pilot hole on the acetabular cage 202. These holes 212 can be used to fasten the acetabular shell 204 to the acetabular bone 206, before the acetabular cage 202 is installed.

The right-hand portion of FIG. 2 shows the acetabular augment 208 positioned between a portion of an acetabular shell 204 and a portion of acetabular bone 206. In some examples, the surgeon can optionally drill one or more holes through the acetabular augment 208, so that an anchor can attach to the acetabular augment 208 or attach to the acetabular bone 206 beneath the acetabular augment 208.

In some examples, the anchor can be provided to the surgeon with the length of suture pre-installed. In other examples, the surgeon or a technician can attach the suture to the anchor. An anchor can be attached to a length of suture in various ways. U.S. Pat. Nos. 8,298,262 and 8,361,113 discuss several ways to attach the suture to a soft anchor. U.S. Pat. Nos. 8,298,262 and 8,361,113 are hereby incorporated by reference in their entirety. For screw anchors, the suture can be positioned in a channel that extends into or along a surface of the anchor, as shown in FIGS. 3 and 4.

Figure 3:
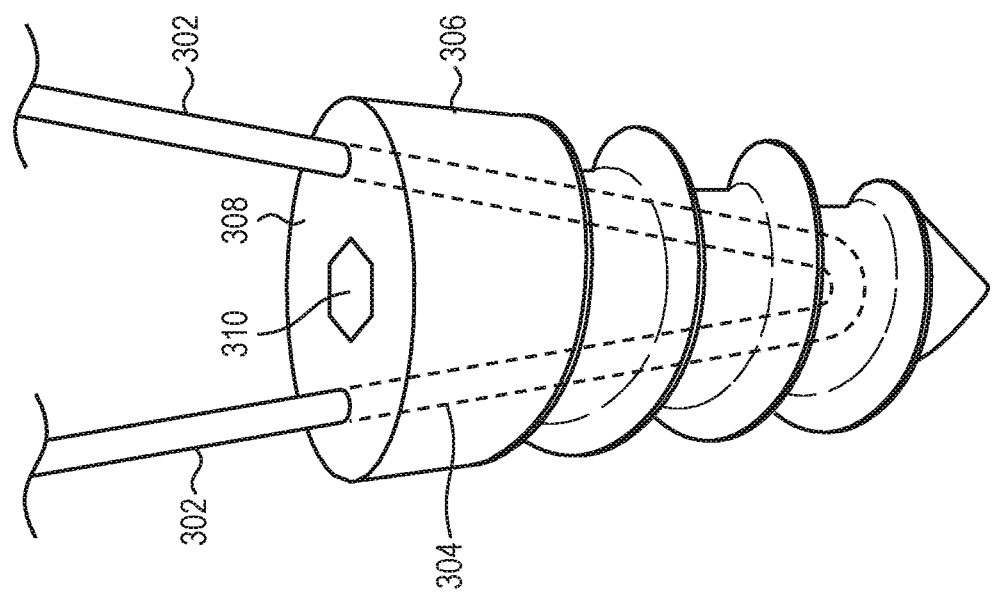
FIG. 3 shows an example of a length of suture positioned in a channel that extends into at least a portion of a screw anchor, in accordance with some examples.

FIG. 3 shows an example of a length of suture 302 positioned in a channel 304 that extends into at least a portion of a screw anchor 306, in accordance with some examples. Polymeric screws can be manufactured relatively easily with such a channel 304. In some examples, the screw anchor 306 can be molded around a portion of the length of suture 302, so that the channel 304 is cross-sectionally sized to match the diameter of the suture 302, and rigidly supports the suture 302. In some examples, the channel 304 can originate at a head 308 of the screw anchor 306, extend into an interior of the screw anchor 306, and return to the head 308 of the screw anchor 306. In some examples, the channel 304 openings in the head 308 of the screw anchor 306 can be positioned on opposite sides of an engagement feature 310, such as a hexagonal opening that can accommodate a hex key.

Figure 4:
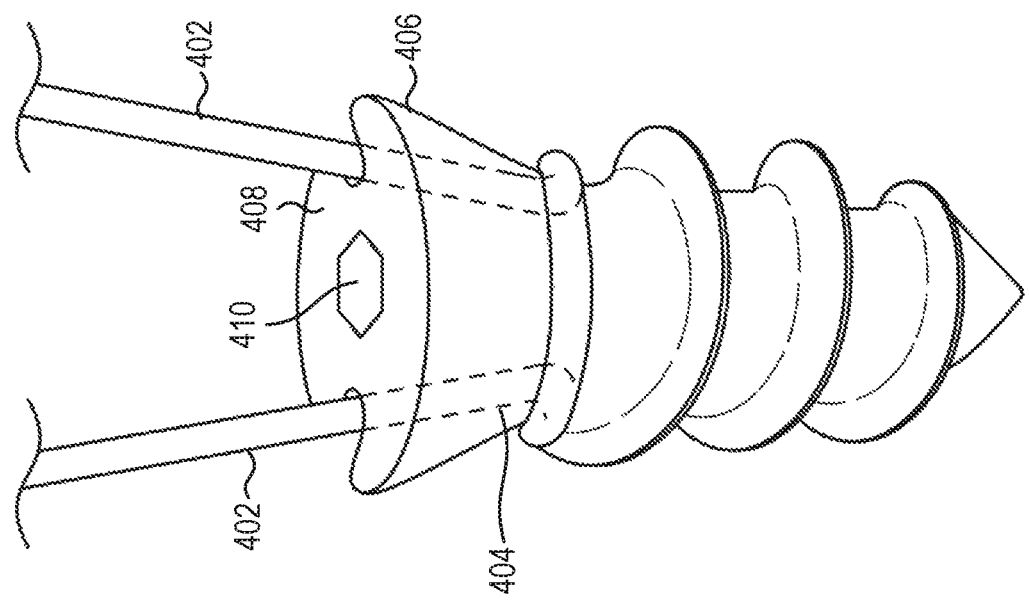
FIG. 4 shows an example of a length of suture positioned in a channel that extends along a surface of a screw anchor, in accordance with some examples.

FIG. 4 shows an example of a length of suture 402 positioned in a channel 404 that extends along a surface of a screw anchor 406, in accordance with some examples. Both polymeric and metallic screws can be manufactured relatively easily with such a channel 404. For these cases, the suture 402 can be attached to the screw anchor 406 after the screw anchor 406 has been manufactured. In some examples, the channel 404 can originate at a head 408 of the screw anchor 406, extend distally along an open-ended channel along a first side of the screw anchor 406, extend circumferentially around the screw anchor 406, extend proximally along an open-ended channel along a second side of the screw anchor 406 opposite the first side, and terminate at the head 408 of the screw anchor 406. In some examples, the channel openings in the head 408 of the screw anchor 406 can be on opposite sides of an engagement feature 410, such as a hexagonal opening that can accommodate a hex key.

Figure 5:
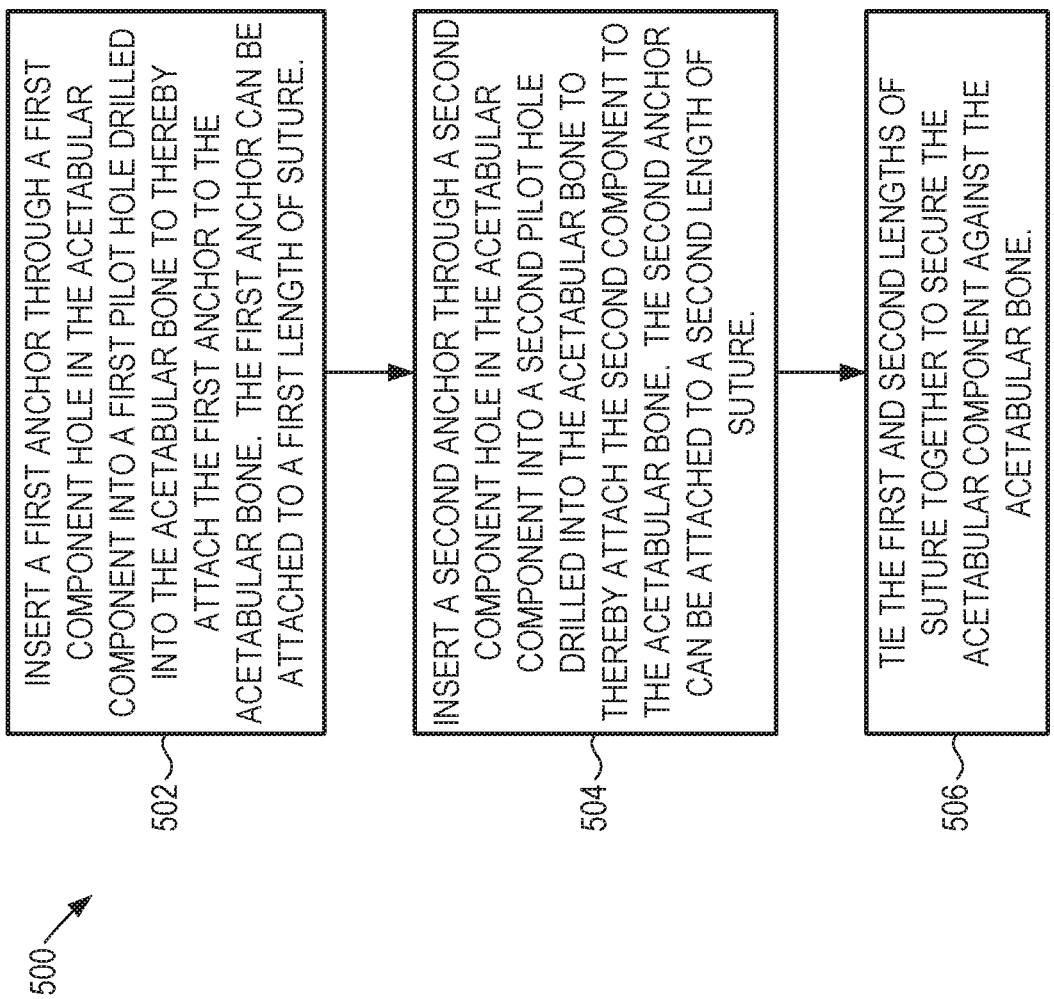
FIG. 5 shows an example of a method for securing an acetabular shell to an acetabular bone, in accordance with some examples.

FIG. 5 shows an example of a method 500 for securing an acetabular shell to an acetabular bone, in accordance with some examples. The method 500 can be executed by a surgeon, using any or all of the acetabular components 102, 202, 204, 208 from FIGS. 1-2, one or more soft anchors, and/or one or both screw anchors 306, 406 from FIGS. 3-4.

At operation 502, the surgeon can insert a first anchor through a first component hole in the acetabular component into a first pilot hole drilled into the acetabular bone to thereby attach the first anchor to the acetabular bone. The first anchor can be attached to a first length of suture before insertion.

At operation 504, the surgeon can insert a second anchor through a second component hole in the acetabular component into a second pilot hole drilled into the acetabular bone to thereby attach the second component to the acetabular bone. The second anchor can be attached to a second length of suture before insertion.

At operation 506, the surgeon can tie the first and second lengths of suture together to secure the acetabular component against the acetabular bone.

In some examples, the surgeon can further position the tied-together first and second lengths of suture in a suture channel formed in the acetabular component. This can help prevent the suture from interfering with the liner, which can later be positioned in the acetabular component. In some examples, such as cemented liner applications that can include revision total hip arthroplasty the surgeon can optionally or alternatively encase the suture in bone cement.

In some examples, one or more screw hole drill guides can be provided for the surgeon. The surgeon can decide whether or not to use such drill guides based on the surgeon's experience, the surgeon's preference, and the particular acetabular shell system being implanted.

In some examples, the surgeon can drill the holes into the acetabular without using a drill guide. For these examples, before inserting the first and second anchors, the surgeon can drill into, but not through, the acetabular bone to form the first pilot hole, and drill into, but not through, the acetabular bone to form the second pilot hole.

In some examples, the surgeon can drill the holes into the acetabular using a drill guide. For these examples, before inserting the first and second anchors, the surgeon can position a screw hole drill guide proximate the acetabular bone, drill through the screw hole drill guide into, but not through, the acetabular bone to form the first pilot hole, drill through the screw hole drill guide into, but not through, the acetabular bone to form the second pilot hole, and remove the screw hole drill guide from the acetabular bone.

In some examples, the acetabular component can include one of an acetabular shell, an acetabular augment, an acetabular shell coupled with an acetabular augment, an acetabular cage, an acetabular shell coupled with an acetabular cage, or an acetabular shell coupled with an acetabular cage and an acetabular augment. Each of these cases is discussed below.

In some examples, the acetabular component can be a press-fit (e.g., non-cemented) acetabular shell. For these examples, when the first and second lengths of suture are tied together, the press-fit acetabular shell can be positioned directly against the acetabular bone. For some of these examples, the first component hole can be a screw hole having a countersink.

In some examples, the acetabular component can be a cemented acetabular shell. For these examples, when the first and second lengths of suture are tied together, a layer of bone cement can be positioned between the cemented acetabular shell and the acetabular bone. For some of these examples, the first component hole can be a screw hole having a countersink.

In some examples, the acetabular component can be an acetabular shell coupled with an acetabular augment. For these examples, when the first and second lengths of suture are tied together, at least a portion of the acetabular augment can be positioned between the acetabular shell and the acetabular bone. For some of these examples, the first component hole can be a screw hole having a countersink.

In some examples, the acetabular component can be an acetabular cage. For these examples, when the first and second lengths of suture are tied together, the acetabular cage can be positioned directly against the acetabular bone. For some of these examples, the first component hole can be an anchor hole lacking a countersink. A liner can be cemented inside the acetabular cage.

In some examples, the acetabular component can be an acetabular shell coupled with an acetabular cage. For these examples, when the first and second lengths of suture are tied together, at least a portion of the acetabular shell is positioned between the acetabular cage and the acetabular bone. For some of these examples, the first component hole can be an anchor hole lacking a countersink.

In some examples, the first and second anchors can be soft anchors that are configured to deform when inserted.

In some examples, the first and second anchors can be formed as polymeric screws. For these examples, the first and second pilot holes can be shaped and sized to accommodate polymeric screws, the first length of suture can be positioned in a first channel that extends along a surface of the first anchor or into at least a portion of the first anchor, and the second length of suture can be positioned in a second channel that extends along a surface of the first anchor or into at least a portion of the second anchor.

In some examples, the first and second anchors can be formed as metallic screws. For these examples, the first and second pilot holes can be sized and shaped to accommodate metallic screws, the first length of suture can be positioned in a first channel that extends along a surface of the first anchor, and the second length of suture can be positioned in a second channel that extends along a surface of the second anchor.

In some examples, the surgeon can additionally remove extra portions of the first and second lengths of suture beyond the knot, twist, or clamp that ties the first and second lengths of suture together.

Figure 6:
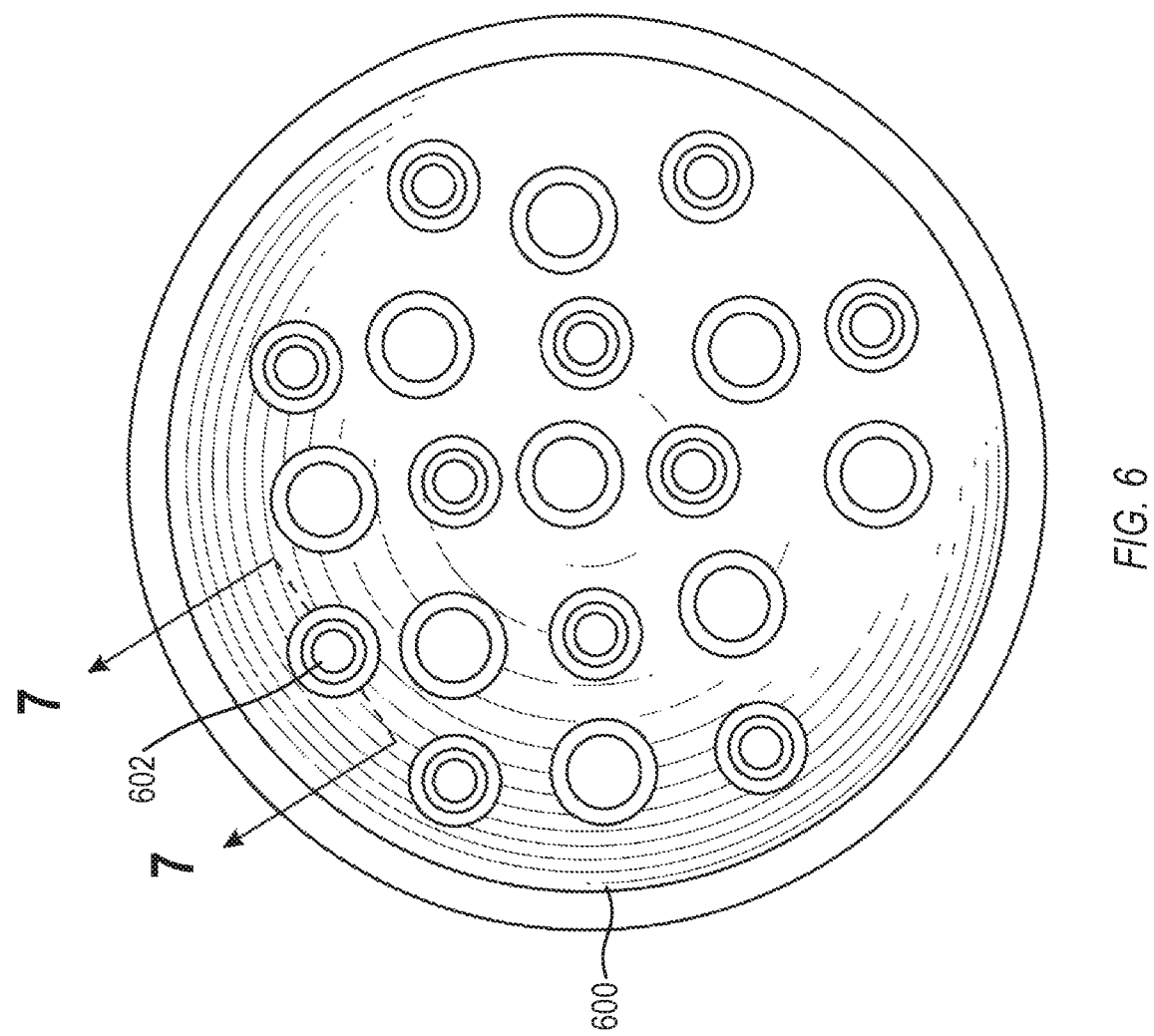
FIG. 6 shows a top view of an example of an acetabular component, in accordance with some examples.
Figure 7:
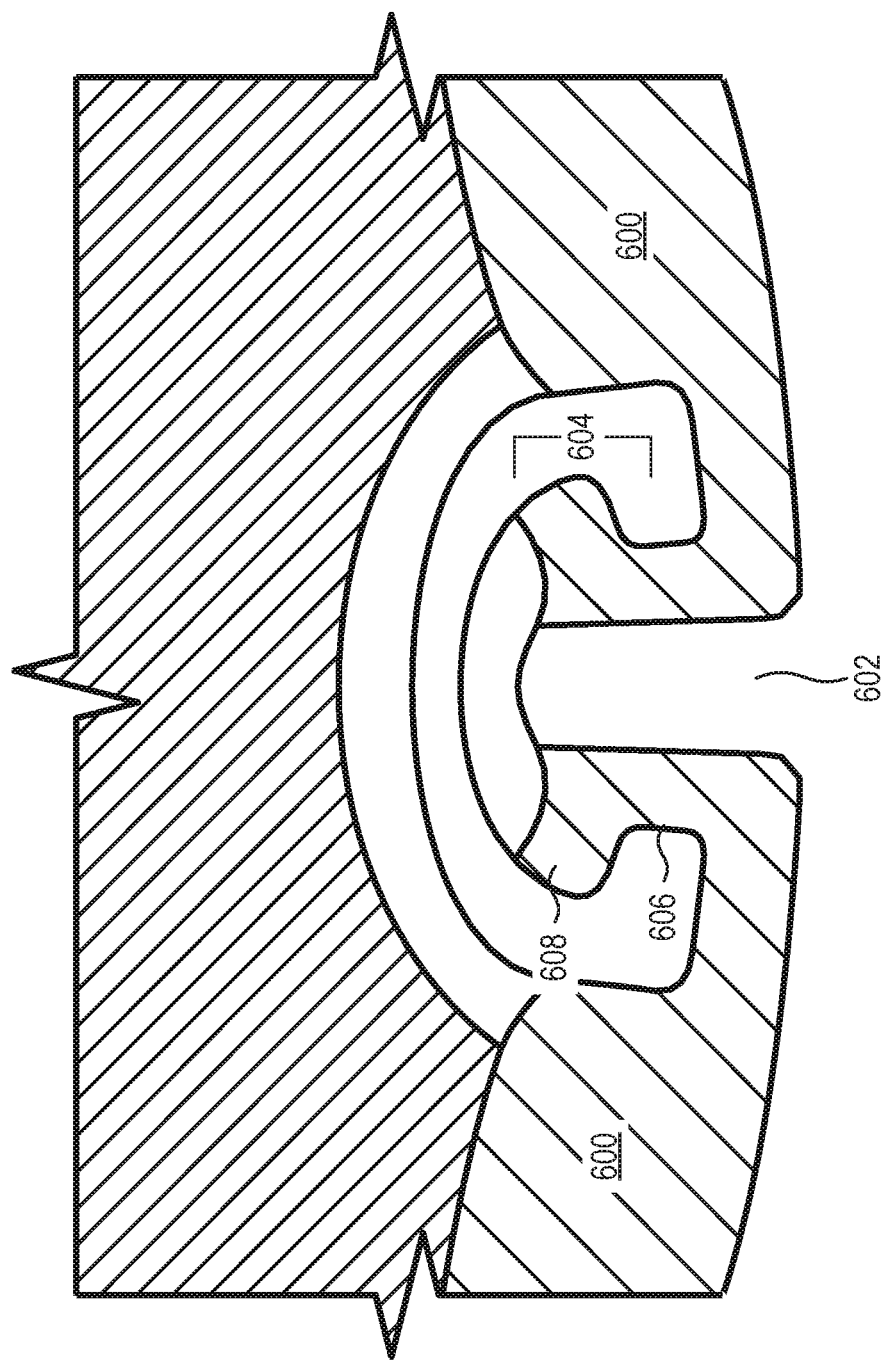
FIG. 7 shows a side-view cross-section of an example of an anchor hole in the acetabular component of FIG. 6, in accordance with some examples.

FIGS. 1-2 above show acetabular components that can include one or more suture channels extending between adjacent holes. Positioning the tied-together suture in the suture channels can prevent the suture from interfering with a liner. FIGS. 6-7 below show an alternate configuration that can also prevent the suture from interfering with a liner.

FIG. 6 shows a top view of an example of an acetabular component 600, in accordance with some examples. FIG. 7 shows a side-view cross-section of an example of an anchor hole 602 in the acetabular component of FIG. 6, in accordance with some examples. The acetabular component 600 can include one of an acetabular shell, an acetabular augment, an acetabular shell coupled with an acetabular augment, an acetabular cage, an acetabular shell coupled with an acetabular cage, or an acetabular shell coupled with an acetabular cage and an acetabular augment.

At least one of the holes in the acetabular component 600 can include a rim feature 604 positioned around the hole 602 to secure the acetabular component 600 against the acetabular bone. The rim feature 604 can include a radially contracted portion 606 that can receive the suture. The rim feature 604 can include a radially expanded portion 608 positioned proximate a first side of the hole 602, where the first side faces away from the acetabular bone when the acetabular component 600 is secured against the acetabular bone. FIG. 6 shows the first side of the hole 602. The radially expanded portion 608 can hold the suture in the radially contracted portion 606. The radially contracted portion 606 can be positioned adjacent the radially expanded portion 608 such that the radially expanded portion 608 is disposed between the radially contracted portion 606 and the first side of the hole 602.

Figure 8:
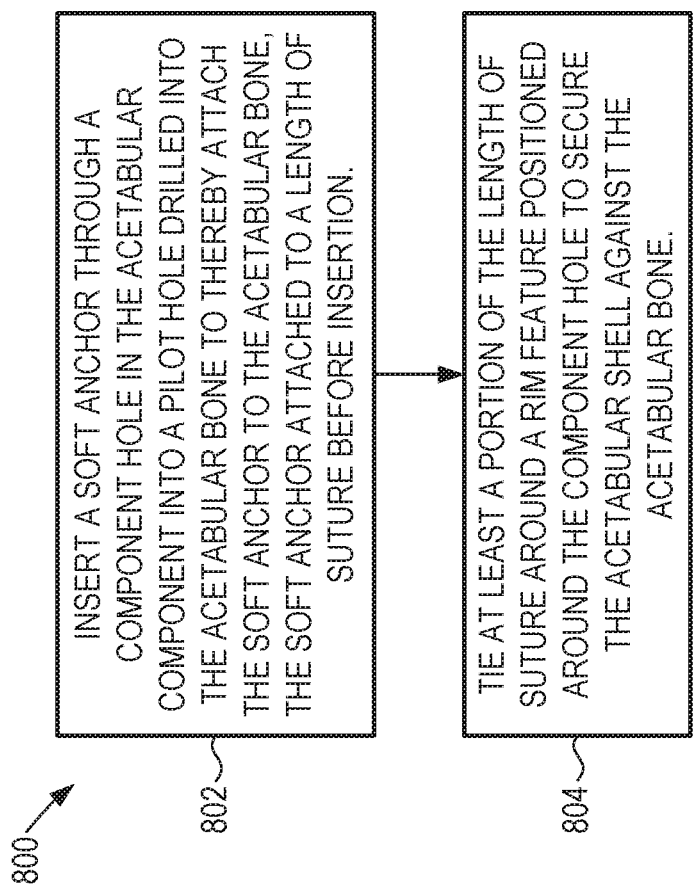
FIG. 8 shows an example of a method for securing an acetabular component to an acetabular bone, in accordance with some examples It should be noted that elements in the drawings are not necessarily drawn to scale. The configurations shown in the drawings are merely examples, and should not be construed as limiting in any manner.

FIG. 8 shows an example of a method 800 for securing an acetabular component to an acetabular bone, in accordance with some examples. The method 600 can be executed by a surgeon, using the acetabular component 600 from FIGS. 6-7, and at least one soft anchor.

At operation 802, the surgeon can insert a soft anchor through a component hole in the acetabular component into a pilot hole drilled into the acetabular bone to thereby attach the soft anchor to the acetabular bone. The soft anchor can be attached to a length of suture before insertion.

At operation 804, the surgeon can tie at least a portion of the length of suture around a rim feature positioned around the component hole to secure the acetabular component against the acetabular bone.

The rim feature shown in FIGS. 6-7 can be used instead of or in addition to the suture channels shown in FIGS. 1-2. In some examples, an acetabular component can include both rim features and suture channels.

To further illustrate the device and related method disclosed herein, a non-limiting list of examples is provided below. Each of the following non-limiting examples can stand on its own, or can be combined in any permutation or combination with any one or more of the other examples.

In Example 1, a method for securing an acetabular component to an acetabular bone can include: inserting a first anchor through a first component hole in the acetabular component into a first pilot hole drilled into the acetabular bone to thereby attach the first anchor to the acetabular bone, the first anchor attached to a first length of suture before insertion; inserting a second anchor through a second component hole in the acetabular component into a second pilot hole drilled into the acetabular bone to thereby attach the second component to the acetabular bone, the second anchor attached to a second length of suture before insertion; and tying the first and second lengths of suture together to secure the acetabular component against the acetabular bone.

In Example 2, the method of Example 1 can optionally additionally include positioning the tied first and second lengths of suture in a suture channel formed in the acetabular component.

In Example 3, the method of any one of Examples 1-2 can optionally further include, before inserting the first and second anchors: drilling into, but not through, the acetabular bone to form the first pilot hole; and drilling into, but not through, the acetabular bone to form the second pilot hole.

In Example 4, the method of any one of Examples 1-3 can optionally further include, before inserting the first and second anchors: positioning a screw hole drill guide proximate the acetabular bone; drilling through the screw hole drill guide into, but not through, the acetabular bone to form the first pilot hole; drilling through the screw hole drill guide into, but not through, the acetabular bone to form the second pilot hole; and removing the screw hole drill guide from the acetabular bone.

In Example 5, the method of any one of Examples 1-4 can optionally be configured such that the acetabular component includes one of an acetabular shell, an acetabular augment, an acetabular shell coupled with an acetabular augment, an acetabular cage, an acetabular shell coupled with an acetabular cage, or an acetabular shell coupled with an acetabular cage and an acetabular augment.

In Example 6, the method of any one of Examples 1-5 can optionally be configured such that the acetabular component is a press-fit acetabular shell; when the first and second lengths of suture are tied together, the press-fit acetabular shell is positioned directly against the acetabular bone; and the first component hole is a screw hole having a countersink.

In Example 7, the method of any one of Examples 1-6 can optionally be configured such that the acetabular component is a cemented acetabular shell; when the first and second lengths of suture are tied together, a layer of bone cement is positioned between the cemented acetabular shell and the acetabular bone; and the first component hole is a screw hole having a countersink.

In Example 8, the method of any one of Examples 1-7 can optionally be configured such that the acetabular component is an acetabular shell coupled with an acetabular augment; when the first and second lengths of suture are tied together, at least a portion of the acetabular augment is positioned between the acetabular shell and the acetabular bone; and the first component hole is a screw hole having a countersink.

In Example 9, the method of any one of Examples 1-8 can optionally be configured such that the acetabular component is an acetabular cage; when the first and second lengths of suture are tied together, the acetabular cage is positioned directly against the acetabular bone; the first component hole is an anchor hole lacking a countersink.

In Example 10, the method of any one of Examples 1-9 can optionally be configured such that the acetabular component is an acetabular shell coupled with an acetabular cage; when the first and second lengths of suture are tied together, at least a portion of the acetabular shell is positioned between the acetabular cage and the acetabular bone; and the first component hole is an anchor hole lacking a countersink.

In Example 11, the method of any one of Examples 1-10 can optionally be configured such that the first and second anchors are soft anchors that are configured to deform when inserted.

In Example 12, the method of any one of Examples 1-11 can optionally be configured such that the first and second anchors are formed as polymeric screws; the first and second pilot holes are sized and shaped to accommodate polymeric screws; the first length of suture is positioned in a first channel that extends along a surface of the first anchor or into at least a portion of the first anchor; and the second length of suture is positioned in a second channel that extends along a surface of the first anchor or into at least a portion of the second anchor.

In Example 13, the method of any one of Examples 1-12 can optionally be configured such that the first and second anchors are formed as metallic screws; the first and second pilot holes are sized and shaped to accommodate metallic screws; the first length of suture is positioned in a first channel that extends along a surface of the first anchor; and the second length of suture is positioned in a second channel that extends along a surface of the second anchor.

In Example 14, the method of any one of Examples 1-13 can optionally additionally include removing extra portions of the first and second lengths of suture beyond the tied-together portions of the first and second lengths of suture.

In Example 15, a method for securing an acetabular component to an acetabular bone can include: inserting a soft anchor through a component hole in the acetabular component into a pilot hole drilled into the acetabular bone to thereby attach the soft anchor to the acetabular bone, the soft anchor attached to a length of suture before insertion; and tying at least a portion of the length of suture around a rim feature positioned around the component hole to secure the acetabular component against the acetabular bone.

In Example 16, the method of Example 15 can optionally be configured such that the rim feature includes: a radially contracted portion configured to receive the suture, the radially expanded portion is positioned proximate a first side of the component hole, the first side facing away from the acetabular bone when the acetabular component is secured against the acetabular bone; and a radially expanded portion configured to hold the suture in the radially contracted portion, the radially contracted portion positioned adjacent the radially expanded portion such that the radially expanded portion is disposed between the radially contracted portion and the first side of the component hole.

In Example 17, the method of any one of Examples 15-16 can optionally additionally include, before inserting the soft anchor: drilling into, but not through, the acetabular bone to form the pilot hole.

In Example 18, the method of any one of Examples 15-17 can optionally be configured such that the hole is an anchor hole lacking a countersink.

In Example 19, a system can include: an acetabular shell configured to attach to an acetabular bone; a first anchor configured to be inserted through a first component hole in the acetabular shell into a first pilot hole drilled into the acetabular bone to thereby attach the first anchor to the acetabular bone; a first length of suture attached to the first anchor; a second anchor configured to be inserted through a second component hole in the acetabular shell into a second pilot hole drilled into the acetabular bone to thereby attach the second anchor to the acetabular bone; a second length of suture attached to the second anchor and configured to be tied to the first length of suture; and a suture channel formed in the acetabular shell and configured to receive the tied first and second lengths of suture.

In Example 20, the system of Example 19 can optionally be configured such that the first and second anchors are soft anchors that are configured to deform when inserted.

What is claimed is:

1. A method for securing an acetabular component to an acetabular bone, the acetabular component including one of an acetabular shell, an acetabular augment, an acetabular shell coupled with an acetabular augment, an acetabular cage, an acetabular shell coupled with an acetabular cage, or an acetabular shell coupled with an acetabular cage and an acetabular augment, the method comprising:
   inserting a first anchor through a first component hole in the acetabular component into a first pilot hole drilled into the acetabular bone to thereby attach the first anchor to the acetabular bone, the first anchor attached to a first length of suture before insertion;
   inserting a second anchor through a second component hole in the acetabular component into a second pilot hole drilled into the acetabular bone to thereby attach the second component to the acetabular bone, the second anchor attached to a second length of suture before insertion; and
   tying the first and second lengths of suture together to secure the acetabular component against the acetabular bone.

2. The method of claim 1, further comprising positioning the tied first and second lengths of suture in a suture channel formed in the acetabular component.

3. The method of claim 1, further comprising, before inserting the first and second anchors:
   drilling into, but not through, the acetabular bone to form the first pilot hole; and drilling into, but not through, the acetabular bone to form the second pilot hole.

4. The method of claim 1, further comprising, before inserting the first and second anchors:
positioning a screw hole drill guide proximate the acetabular bone;
drilling through the screw hole drill guide into, but not through, the acetabular bone to form the first pilot hole;
drilling through the screw hole drill guide into, but not through, the acetabular bone to form the second pilot hole; and
removing the screw hole drill guide from the acetabular bone.

5. The method of claim 1, wherein:
the acetabular component is a press-fit acetabular shell;
when the first and second lengths of suture are tied together, the press-fit acetabular shell is positioned directly against the acetabular bone; and
the first component hole is a screw hole having a countersink.

6. The method of claim 1, wherein:
the acetabular component is a cemented acetabular shell;
when the first and second lengths of suture are tied together, a layer of bone cement is positioned between the cemented acetabular shell and the acetabular bone; and
the first component hole is a screw hole having a countersink.

7. The method of claim 1, wherein:
the acetabular component is an acetabular shell coupled with an acetabular augment;
when the first and second lengths of suture are tied together; at least a portion of the acetabular augment is positioned between the acetabular shell and the acetabular bone; and
the first component hole is a screw hole having a countersink.

8. The method of claim 1, wherein:
the acetabular component is an acetabular cage;
when the first and second lengths of suture are tied together, the acetabular cage is positioned directly against the acetabular bone;
the first component hole is an anchor hole lacking a countersink.

9. The method of claim 1, wherein:
the acetabular component is an acetabular shell coupled with an acetabular cage;
when the first and second lengths of suture are tied together, at least a portion of the acetabular shell is positioned between the acetabular cage and the acetabular bone; and
the first component hole is an anchor hole lacking a countersink.

10. The method of claim 1, wherein the first and second anchors are soft anchors that are configured to deform when inserted.

11. The method of claim 1, wherein:
the first and second anchors are formed as polymeric screws;
the first and second pilot holes are sized and shaped to accommodate polymeric screws;
the first length of suture is positioned in a first channel that extends along a surface of the first anchor or into at least a portion of the first anchor; and
the second length of suture is positioned in a second channel that extends along a surface of the first anchor or into at least a portion of the second anchor.

12. The method of claim 1, wherein:
the first and second anchors are formed as metallic screws;
the first and second pilot holes are sized and shaped to accommodate metallic screws;
the first length of suture is positioned in a first channel that extends along a surface of the first anchor; and
the second length of suture is positioned in a second channel that extends along a surface of the second anchor.

13. The method of claim 1, further comprising removing extra portions of the first and second lengths of suture beyond the tied-together portions of the first and second lengths of suture.

14. A method for securing an acetabular component to an acetabular bone, the method comprising:
inserting a soft anchor through a component hole in the acetabular component into a pilot hole drilled into the acetabular bone to thereby attach the soft anchor to the acetabular bone, the soft anchor attached to a length of suture before insertion; and
tying at least a portion of the length of suture around a rim feature positioned around the component hole to secure the acetabular component against the acetabular bone.

15. The method of claim 14, wherein the rim feature includes:
a radially contracted portion configured to receive the suture, the radially expanded portion is positioned proximate a first side of the component hole, the first side facing away from the acetabular bone when the acetabular component is secured against the acetabular bone; and
a radially expanded portion configured to hold the suture in the radially contracted portion, the radially contracted portion positioned adjacent the radially expanded portion such that the radially expanded portion is disposed between the radially contracted portion and the first side of the component hole.

16. The method of claim 14, further comprising, before inserting the soft anchor:
drilling into, but not through, the acetabular bone to form the pilot hole.

17. The method of claim 14, herein the hole is an anchor hole lacking a countersink.

18. A system, comprising:
an acetabular shell configured to attach to an acetabular bone;
a first anchor configured to be inserted through a first component hole in the acetabular shell into a first pilot hole drilled into the acetabular bone to thereby attach the first anchor to the acetabular bone;
a first length of suture attached to the first anchor;
a second anchor configured to be inserted through a second component hole in the acetabular shell into a second pilot hole drilled into the acetabular bone to thereby attach the second anchor to the acetabular bone;
a second length of suture attached to the second anchor and configured to be tied to the first length of suture; and
a suture channel formed in the acetabular shell and configured to receive the tied first and second lengths of suture.

19. The system of claim 18, wherein the first and second anchors are soft anchors that are configured to deform when inserted.

* * * * *